United States Patent [19]

Voyt

[11] 4,144,325
[45] Mar. 13, 1979

[54] METHOD OF AND COMPOSITION FOR PREVENTING SUNBURN WHILE AFFORDING TANNING

[76] Inventor: Walter F. Voyt, Rte. 1, Box 43, Elwood, Ill. 60421

[21] Appl. No.: 740,646

[22] Filed: Nov. 10, 1976

[51] Int. Cl.$^2$ .................. A61K 7/42; A61K 7/44; A61K 31/355

[52] U.S. Cl. ..................................... 424/59; 424/60; 424/284

[58] Field of Search ..................... 424/59, 284, 60

[56] References Cited

U.S. PATENT DOCUMENTS

| | | | |
|---|---|---|---|
| 2,895,878 | 7/1959 | Lehman | 424/284 X |
| 3,458,637 | 7/1969 | Schlegel et al. | 424/284 X |
| 3,803,179 | 4/1974 | Ahrens | 424/284 |
| 3,825,563 | 7/1974 | Ahrens | 424/284 |

FOREIGN PATENT DOCUMENTS

| | | | |
|---|---|---|---|
| 1492025 | 12/1969 | Fed. Rep. of Germany | 424/284 |
| 2144249 | 3/1972 | Fed. Rep. of Germany | 424/284 |
| 2358740 | 5/1975 | Fed. Rep. of Germany | 424/59 |
| 1239965 | 7/1971 | United Kingdom | 424/284 |

*Primary Examiner*—Dale R. Ore
*Attorney, Agent, or Firm*—Neuman, Williams, Anderson & Olson

[57] ABSTRACT

A method of and composition for preventing erythema of the skin caused by the absorption of burning ultraviolet radiation resulting from exposure to natural or artificial sources thereof while concomitantly allowing tanning of the skin is provided, consisting of the application of a sunscreen composition demonstrating selective ultraviolet radiation absorption in the 295–315 nanometer wavelength range prior to exposure of the skin to said radiation source, said composition comprising a sunscreen-effective amount of an ultraviolet-absorbing tocopherol compound selected from the group consisting of alpha tocopherol, beta tocopherol, gamma tocopherol, delta tocopherol, epsilon tocopherol, zeta tocopherol, eta tocopherol and mixtures thereof, and an inert carrier vehicle, said vehicle being non-toxic and non-irritating to the skin.

26 Claims, No Drawings

METHOD OF AND COMPOSITION FOR PREVENTING SUNBURN WHILE AFFORDING TANNING

BACKGROUND OF THE INVENTION

1. Field of the Invention

This invention relates generally to the prevention of erythema of the skin caused by the absorption of burning ultraviolet radiation while concomitantly allowing tanning of the skin, and more particularly relates to sunscreen compositions having ideal properties for such purpose.

2. Description of the Prior Art

Extensive studies have been made of the ultraviolet radiation of sunlight and skylight reaching the surface of the earth and the effects of such radiation on the human skin. It has been established that the radiation between 295 and 315 nanometers produces substantially all of the erythemal energy and a substantial portion of the tanning energy with a maximum erythemal effect being demonstrated at 296.7 nanometers. Radiation between 315 and 400 nanometers, the near ultraviolet, is pigmentogenic but not erythemogenic, and promotes incident tanning. The differing intensities and the erythemal and tanning effectiveness of the various wavelengths within these ranges have been established and methods have been determined for calculating accurately their effects on normal untanned skin.

The only practical technique for preventing sunburn is to limit the exposure of the skin to the erythemogenic range of sunlight and skylight radiation to dosages less than those required to produce burning. This may be accomplished by avoiding exposure of the individual for more than the shortest periods of time. Such limitations do not, however, fit into the designs of a civilization which enjoys outdoor activity and admires melanization of the skin through insolation. Avoidance of exposure is not necessary because the effects of the exposure may be mitigated readily by the use of an ultraviolet screening agent which, applied to the skin, attenuates the dosage of erythemogenic radiation reaching the skin.

Products containing ultraviolet screening agents are generally evaluated on the basis of exposure to summer noon-time sun for a four-hour period, the total erythemal flux of such exposure being limited by the ultraviolet screen to provide the desired degree of protection and tanning with safety. To provide fast tanning with minimal protection, approximately 10–18% of the total erythemal flux of sunlight and skylight should reach the skin in the four-hour period. For regular protection and tanning, 6–12% of the total erythemal flux should reach the skin. For extra protection, only 1–6% of the total flux should reach the skin, while less than 1% should be allowed to reach the skin where a total blocking effect is desired.

Approximately 76% of the physiological tanning potential of sunlight is found in the ultraviolet region between 295 and 315 nanometers, the erythemal area. The balance is found in the range between 315 and 400 nanometers, the tanning area. The erythemal limitations necessarily control the amount of tanning which may be obtained from the ultraviolet in the erythemal area, but there is no limitation on the availability of tanning from the ultraviolet in the incident tanning area since there is no appreciable erythemal effect. To provide the desired amount of protection and/or tanning, then, ultraviolet screens can be utilized to furnish the required erythemal flux transmission by adjustment of the percentage of such screen used.

There are many other properties necessary for an ideal sunscreening agent besides having the proper ultraviolet absorption characteristics. These can be listed as follows:

(1) the screening agent should demonstrate a relatively sharp absorption cutoff at 315 nanometers so that it transmits the desired tanning radiation at wavelengths above the erythemal range;
(2) the screening agent should show resistance to chemical and photochemical changes in structure which decrease its ultraviolet absorbant effectiveness;
(3) the screening agent should not be easily absorbed through the skin or cause any pathological side effects such as primary irritation, inducing sensitivity or allergic response, should not impede melanogenesis, should not induce any trophic changes in the skin, and should not interfere with any normal growth or metabolic processes of the skin and mucous membranes and associated organs;
(4) the screening agent should be relatively insoluble in water and perspiration, while being sufficiently oil and solvent soluble for versatility in formulating in a variety of vehicles and for stability in oil-water emulsions;
(5) the screening agent should be of such a character that it is capable of forming continuous films on the skin when applied by itself or in a convenient carrier vehicle for uniform protective effect;
(6) the screening agent should exhibit no odor or its odor should be easily masked so as not to interfere with the perfuming of a product; and
(7) the screening agent should exhibit little residual staining to skin and clothing, especially in the presence of sunlight, heat, laundry detergents, perspiration and the like.

Sunscreen agents in common use fail to exhibit one or more of the desired properties set forth above. These agents consist of individual species or mixtures of the salicylates, para-aminobenzoates, cinnamates, naphthoates, gallates and benzophenones:

(a) The salicylates have the disadvantage of screening out a considerable portion of the rays in the tanning region, particularly in the 315–330 nanometer range. Additionally, they exhibit a low absorptive capacity which requires the use of high concentrations in order to be effective. Many salicylates exhibit a highly undesirable odor level and a pronounced analgesic and numbing effect when applied to the skin. Their oil solubility is also rather limited in most cases.

(b) The para-aminobenzoates also have the disadvantages of having an analgesic and numbing effect on application to the skin. Para-aminobenzoic acid, which has poor overall solubility, lends itself to alteration by esterification with the proper alcohol to produce solubilities of the desired nature to a limited extent. Such aminobenzoate esters, however, have the great disadvantage of imparting a high degree of yellow to brown permanent stain to fabrics, e.g. clothing, beachwear, and towels, especially in the presence of or on exposure to ultraviolet light. Additionally, high-melting aminobenzoates readily crystallize on the skin and neither form a continuous film nor adhere well enough to afford satisfactory protection. The aminobenzoates also demonstrate a gradual cutoff resulting in the screening out of rays in the tanning region, particularly between 315–340 nanometers.

(c) The naphthoates have poor solubility characteristics, an overly broad absorptive spectrum, and low absorptivities.

(d) The cinnamates demonstrate good absorptivities, good solubilities and exhibit little staining. Their absorption maxima, however, do not extend far enough into the erythemal range, while they exhibit a decided cutoff in the tanning region between 315–345 nanometers. Additionally, when the esters of cinnamic acid are derivatives of volatile alcohols, the resulting cinnamate tends to be an irritant and often has a high odor. Other substituted cinnamate esters produce a distinct sensation of warming around the nostrils and eyelids when first applied, a sensation which many users find unpleasant and which often presages irritation. Forming esters of high molecular weight or low volatility reduces these irritant/odor tendencies to a satisfactory level but also reduces the sun-screening efficiency by lowering the absorptivity.

(e) The benzophenones tend to crystallize readily on the skin, and neither form a continuous film nor adhere well enough to afford satisfactory protection, while benzalacetophenone demonstrates marked irritant effects. Additionally, the benzophenones demonstrate a wide absorption spectrum which includes not only the erythemogenic wavelengths but also the pigmentogenic or tanning wavelengths.

None of the sunscreens known to the art, then, provide the optimum combination of properties desirable for use in preventing erythema of the skin from exposure to sunlight and skylight while concomitantly affording tanning of the skin, all of said prior art screens exhibiting one or more undesirable properties for such use.

SUMMARY OF THE INVENTION

The present invention relates to a method of and composition for preventing erythema of the skin caused by the absorption of burning ultraviolet radiation resulting from exposure to natural or artificial sources thereof while concomitantly allowing tanning of the skin. The method consists of the application of a sunscreen composition demonstrating selective ultraviolet radiation absorption in the 295–315 nanometer wavelength range prior to exposure of the skin to the radiation source. The sunscreen composition comprises a sunscreen-effective amount of an ultraviolet-absorbing 6-chromanol derivative compound of the formula

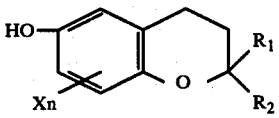

wherein $R_1$ is selected from the group consisting of hydrogen and alkyl; $R_2$ is selected from the group consisting of hydrogen, alkyl and alkenyl; X is an alkyl group; and n is an integer from one to three; and an inert carrier vehicle for said compound, the vehicle being non-toxic and non-irritating to the skin. More particularly, the sunscreen composition comprises a sunscreen-effective amount of a tocol derivative compound of the formula

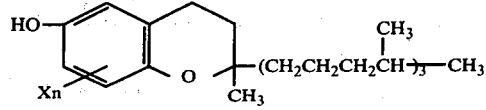

wherein X is an alkyl group, and n is an integer from one to three.

The present invention overcomes the drawbacks of the prior art by providing a method of and composition for preventing erythema while allowing tanning wherein the sunscreen agent demonstrates the desired erythemal-range ultraviolet absorption properties while possessing a relatively sharp absorption cutoff at 315 nanometers to minimize absorption of the desired tanning radiation at wavelengths above the erythemal range, and which further possesses good resistance to chemical and photochemical changes in structure which decrease its erythemal range absorbancy, is not easily absorbed through the skin, causes no irritation, sensitization or other trophic changes in the skin, is insoluble in water and perspiration while demonstrating good oil and solvent solubility, forms a continuous film when applied to the skin, has a pleasant odor, and exhibits no residual staining to skin and clothing.

Accordingly, it is an object of this invention to provide an improved method of preventing erythema of the skin caused by the absorption of burning ultraviolet light while concomitantly allowing tanning of the skin.

It is a further object of the invention to provide a sunscreen composition which prevents erythema of the skin caused by the absorption of burning ultraviolet light while concomitantly allowing tanning of the skin.

It is another object of this invention to provide a sunscreen composition which demonstrates a sharp absorption cutoff at 315 nanometers such that it transmits a maximum of the desired tanning radiation at wavelengths above the erythemal range.

It is a further object of this invention to provide a sunscreen composition which additionally demonstrates good resistance to chemical and photochemical changes in structure which decrease its erythemal range absorbancy, is not easily absorbed through the skin, causes no irritation, sensitization or other trophic changes in the skin, is insoluble in water and perspiration while demonstrating good oil and solvent solubility, forms a continuous film when applied to the skin, has a pleasant odor, and exhibits no residual staining to skin and clothing.

Other objects and advantages of this invention will become apparent upon reading the following detailed description and appended claims.

DESCRIPTION OF THE PREFERRED EMBODIMENT

The preferred method of the invention provides for the prevention of erythema of the skin caused by the absorption of burning ultraviolet radiation resulting from exposure to natural or artificial sources thereof while concomitantly allowing tanning of the skin by the application of a sunscreen composition demonstrating selective ultraviolet radiation absorption in the 295–315 nanometer wavelength range prior to exposure of the skin, said sunscreen composition comprising a sunscreen-effective amount of an ultraviolet-absorbing tocol derivative compound of the formula

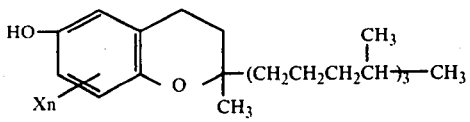

wherein X is an alkyl group, and n is an integer from one to three.

The particularly preferred compounds for use in the sunscreen composition and method of the invention are the tocopherols, which comprise the monomethyl, dimethyl or trimethyl derivates of tocol having the following formula:

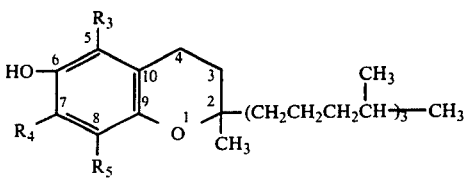

wherein $R_3$, $R_4$ and $R_5$ are selected from the group consisting of hydrogen and methyl, at least one of said substituents being a methyl group, such compounds being denominated as follows:

| alpha tocopherol | 5,7,8-trimethyl tocol |
|---|---|
| beta-tocopherol | 5,8-dimethyl tocol |
| gamma tocopherol | 7,8-dimethyl tocol |
| delta tocopherol | 8-methyl tocol |
| epsilon tocopherol | 5-methyl tocol |
| zeta tocopherol | 5,7-dimethyl tocol |
| eta tocopherol | 7-methyl tocol |

Alpha, beta, gamma and delta tocopherol comprise the traditional tocopherols, all of which demonstrate in vivo vitamin E activity. Epsilon, zeta and eta are newly discovered tocopherol compounds, and would also be expected to demonstrate vitamin E activity.

It is known that the tocopherols demonstrate ultraviolet absorptivity. Alpha tocopherol exhibits an absorption maxima at 294 nanometers; beta, gamma and delta tocopherol exhibit absorption maxima at 297-98 nanometers, while epsilon demonstrates a maxima at 296 nanometers, zeta at 292 nanometers, and eta at 298 nanometers. It is also known that the tocopherols exhibit strong antioxidant properties, particularly the beta, gamma and delta tocopherols. It is this combination of the exhibition of absorption maxima centered within the erythemal region and strong antioxidant properties that provides the marked advantages over prior art sunscreen agents when the tocopherols are incorporated into the composition of the invention.

It should be particularly noted that major property differences exist between the pure tocopherols and other related compounds which exhibit vitamin E activity. This is particularly true with respect to alpha tocopherol acetate, which is found in a wide variety of cosmetic preparations. While alpha tocopherol acetate exhibits the same in vivo nutritive properties as alpha tocopherol, it exhibits virtually no antioxidant properties, and its absorption maxima of 285.5 nanometers is well below the erythemal range. The acetate form, then, has neither the necessary absorbance nor the desirable antioxidant properties for use as a sunscreen exhibited by the pure tocopherols.

The various types of tocopherols which are found in nature occur largely in plants, with only a minimum quantity being present in animal tissue. Wheat germ oil and other seed oils are generally considered to have the highest concentration of tocopherols of any oils. Naturally occurring tocopherol levels in oils vary from a low of 3 mg/100 gm for coconut oil to a high of 500 mg/100 gm of wheat germ oil, comprising ½% by weight. In noonday sunlight, a minimal perceptible erythema (MPE) will result after 17.6 minutes exposure. An acceptable sunscreen should provide at least 1½ to 2 hours of exposure in noonday sun without a minimum perceptible erythema resulting. The application of a preparation containing mixed tocopherols in the same concentration as found in wheat germ oil (½%) to the skin will provide, when applied in the same average thickness as a sunscreen composition (0.025 mm), protection from a minimal perceptible erythema for 22.6 minutes, well below that acceptable in the art for a sunscreen composition.

The preferred tocopherol compounds are readily available commercially in two forms, either as pure alpha tocopherol, or as a mixture of tocopherols derived from seed oils and comprising predominantly alpha, beta, gamma and delta tocopherol. The composition of the invention is prepared by combining the tocopherol compound in a sunscreen-effective amount with an inert carrier vehicle, which vehicle is non-toxic and non-irritating to the skin. Any of the well-known cosmetic vehicles may be utilized, including water, mineral oils, vegetable oils, petrolatum, alcohols and mixtures thereof. The high antioxidant strength of the tocopherols allows the use of unsaturated as well as saturated vegetable oils (such as coconut oil), including such oils as olive oil, corn oil, cottonseed oil, soybean oil and the like. The vehicle may be in a liquid form such as a tanning oil or it may be in a highly viscous form such as tanning gel or butter.

The composition must include a sunscreen-effective amount of the tocopherol compound utilized. For a fast tanning composition, at least about 10 to 25% by weight alpha tocopherol should be included, while at least about 4.5 to 10% by weight of a mixture consisting essentially of alpha, beta, gamma and delta tocopherol should be utilized. As more protection is required, the amount of tocopherol within the composition is increased. For a regular tanning composition, at least about 20 to 40% by weight alpha tocopherol should be included, while an extra protection composition should contain at least about 50 to 80% by weight alpha tocopherol. Similarly, if a mixture consisting essentially of alpha, beta, gamma and delta tocopherols is utilized, a regular tanning composition should contain at least 7 to 17% by weight of the tocopherol mixture, while an extra protection composition should contain at least about 20 to 70% by weight.

Due to their unique combination of erythemal-range ultraviolet absorption and antioxidant properties, the tocopherols may be utilized in the composition of the invention without the need for incorporation of an additional antioxidant. The tocopherols exhibit slow oxidation when exposed to oxygen and light, maintaining their erythemal-range absorption effectiveness and remaining sufficiently stable to provide sunscreening action for at least 8 hours. Antioxidants may be incorporated into the composition of the invention, if desired, to extend the life of the tocopherols. Useful antioxidants include butylated hydroxytoluene, butylated hydroxyanisole, propyl gallate and the like when incorporated in effective concentrations. Additional stabilizers may also be incorporated to increase tocopherol life with respect to exposure to metal salts, particularly ferric salts. Metal chelating agents which comprise antioxidant synergists are particularly useful and may be incorporated in the composition of the invention. Such agents include triethanol amine and its fatty acid salts, isopropylamine and its fatty acid salts, ethylenediaminetetraacetic acid and its disodium salt, citric acid and its fatty acid esters, ascorbic acid and its fatty acid esters and the like.

Antimicrobial agents may also be included in the composition of the invention to reduce the growth of bacteria, molds, fungi and the like. The alkyl parabens are the preferred antimicrobials for incorporation into the composition of the invention, particularly methyl and propyl paraben.

Additional components well known to the cosmetic art may also be incorporated in the composition of the invention. Emulsifiers, perfumes and coloring agents may be included, as may extending components such as waxes, petrolatum and silicone oils, which reduce skin absorption of the tocopherols. Preferably the composition of the invention should contain from about 50 to 600% by weight of tocopherol of any such extending component.

The tocopherols are practically insoluble in water, while freely soluble in oils, fats, acetone, alcohol and other solvents. As such, they may be readily formulated with standard cosmetic carrier vehicles. When spread on the skin in a thin layer, the tocopherols exhibit excellent resistance to removal by water and perspiration. Their oil and solvent solubility further provides for stability when formulated into an oil-water emulsion according to this invention.

The composition of the invention provides a number of other advantages over prior art sunscreens. The tocopherols are non-irritating to the skin, and present no toxicity problem with respect to skin absorption; there is no evidence that a state of hypervitaminosis can be produced by excessive dosages of the tocopherols. Studies have shown that the tocopherols prevent degradation of sebum and cellular fats by oxidation, and may serve to slow cellular aging by virtue of their antioxidant properties. The composition of this invention also provides an additional function where applied to previously sunburned skin: due to their antioxidant properties, the tocopherols when applied in a thin film will provide a chemical oxygen barrier on the skin. This isolates the skin from oxygen, which enhances the healing of the burn, while interferring less with the functions of the sweat and sebaceous glands than does the use of a mineral oil or petroleum jelly.

The composition of the invention exhibits none of the detrimental tendency to stain the skin or clothing prevalent with respect to prior art sunscreens, as the tocopherols form colored degradation products only after extreme exposure to oxygen and light. No odor problem is presented by the composition, as the tocopherols have a low, pleasant odor. Additionally, the tocopherols are capable of forming continuous films on the skin on evaporation of volatile carriers, and are otherwise film forming when incorporated into oils, emulsions and gels.

The composition of the invention exhibits ideal absorption and cutoff properties superior to those of the prior art sunscreens. The absorption maxima of the tocopherols are grouped in the 294–298 nanometer range, which corresponds to the most erythemally-effective part of the ultraviolet range, which falls at 297 nanometers. Of particular advantage, however, is the narrowness of the absorption maxima, and the sharp cutoff peak in the 315 nanometer range. The effect of this sharp peak is demonstrated by comparing the amount of tanning transmission afforded by a screening composition which provides four hours of exposure with 7% erythemal transmission (which will protect a user against a painful erythemal dose) of the composition of the invention with that afforded by prior art sunscreen compositions.

Table 1

| Sunscreen | Weight percentage of screen necessary to provide 7% erythemal transmission | Corresponding percent tanning transmission |
|---|---|---|
| Glyceryl p-aminobenzoate | 2.0 | 87.0 |
| Isoamyl N,N-p-dimethyl aminobenzoate | 1.3 | 71.0 |
| Homomenthyl salicylate | 11.0 | 68.0 |
| 2-ethoxyethyl-p-methoxycinnamate | 1.4 | 51.0 |
| Alpha tocopherol | 34.0 | 93.0 |
| Mixed tocopherol | 15.0 | 94.0 |

As may be seen from Table 1, the composition of the invention provides superior tanning transmission when compared to the prior art sunscreen agents.

Also in accordance with the invention is the method of preventing sunburn utilizing a sunscreen composition which comprises a sunscreen-effective amount of an agent consisting of at least 50% by weight of an ultraviolet-absorbing tocopherol compound as a major component and a non-tocopherol ultraviolet-absorbing compound as a minor component. The non-tocopherol ultraviolet-absorbing compound may be selected from the group consisting of the ultraviolet-absorbing salicylates, such as menthyl or homomenthyl salicylate (homosalate), the paraaminobenzoates, such as glyceryl p-aminobenzoate, isoamyl N,N-p-dimethylaminobenzoate, and amyl-p-dimethylaminobenzoate, the benzophenones, the naphthoates, the gallates, the cinnamates, such as 2-ethoxyethyl-p-methoxycinnamate, and mixtures thereof. The tocopherol component may comprise either alpha tocopherol or mixed tocopherols and should comprise at least 50% by weight of the sunscreen agent. The same carrier vehicles effective for use with the tocopherol compounds may be utilized with such sunscreen components, as may the same antioxidants, antimicrobials and extenders.

For a fast tanning composition utilizing a tocopherol and non-tocopherol compound combination as the sunscreen agent, at least about 5 to about 13% by weight alpha tocopherol should be included, while at least about 2.3 to 5% by weight of a mixture consisting essentially of alpha, beta, gamma and delta tocopherol should be utilized. As more protection is required, the amount of sunscreen agent within the composition is increased, concomitantly increasing the quantity of tocopherol. For a regular tanning composition, at least about 10 to about 20% by weight alpha tocopherol should be included while an extra protection composition should contain at least about 25 to 50% by weight alpha tocopherol. Similarly, if a mixture consisting essentially of alpha, beta, gamma and delta tocopherols is utilized, a regular tanning composition should contain at least 3.5 to 9% by weight of the tocopherol mixture, while an extra protection composition should contain at least about 10 to 50% by weight.

The following examples illustrate the method and composition of the invention:

EXAMPLE 1

Comparison of absorption spectra of alpha tocopherol, mixed tocopherol, and alpha tocopherol acetate A sample of mixed tocopherols denominated as Covi-Ox T-50 was obtained from General Mills Chemicals, Incorporated, Minneapolis, Minnesota. Covi-Ox T-50 is assayed to assure a 50% tocopherol content, but may contain as much as 55%. At least 75% of the tocopherol content is composed of the non-alpha tocopherols (predominantly beta, gamma, and delta), the remaining 45–50% of the sample being soybean oil.

263 mg of this sample were weighed into a 100-ml volumetric flask. Isopropyl alcohol was added to make to volume. After dissolving in the alcohol, 10 ml of the solution was pipetted into a 100-ml volumetric flask. Isopropyl alcohol was added to this second flask to bring the volume to 100 ml, the solution now containing 26.3 mg of sample per 100 ml of alcohol.

Absorbances were then measured utilizing a Beckman DU-2 ultraviolet spectrophotometer equipped with a line-operated AC power supply. The following instrument operating parameters were held constant in each measurement:

Source: Beckman deuterium lamp
Load resistor: Photo multiplier
Slit: 0.2 mm
Phototube: Ultraviolet sensitive, 190–700 nm
Cells: Two matched 1-cm rectangular silica cells
Temperature: Ambient Wavelength accuracy was maintained by calibrating the monochrometer against the known emission lines of a mercury lamp.

The sample was poured into a 1-cm silica cell. The absorbance of the solution was measured between 400 and 270 nanometers on the Beckman spectrophotometer using isopropyl alcohol in a 1-cm cell as a blank. The absorbancy of the sample was then calculated from the absorbance as follows:

$$E_{1\ cm}^{1\%} = \text{absorbancy} = (A/B) \times C \times (D/E),$$

where
A = 1000 mg/100 ml
B = 26.3 mg/100 ml
C = absorbance
D = 100%
E = 55% mixed tocopherols in the sample These values are set out in Table A. The experimental data agrees well with the published absorbancy of tocopherols as given in the *Merck Index*, where alpha = 71–76 at 294 nm, beta = 86.4 at 297 nm, gamma = 92.8 at 298 nm, and delta = 91.2 at 298 nm.

A sample of pure dl-alpha tocopherol was also obtained from Hoffman-LaRoche, Inc., Nutley, New Jersey, said sample being certified to contain 1000 mg of dl-alpha tocopherol per gram.

The sample was prepared for absorbance measurements as above, save that 15.7 mg of sample per 100 ml of alcohol was used for absorbance measurements. The absorbancy of the sample was then calculated from the absorbance as follows:

$$E_{1\ cm}^{1\%} = \text{absorbancy} = (A/B) \times C,$$

where
A = 1000 mg/100 ml
B = 15.7 mg/100 ml
C = absorbance

These values are set out in Table A. The experimental data agrees well with the published absorbancy of dl-alpha tocopherol as given in the *Merck Index*, where alpha = 71–76 at 294 nm.

Additionally, a sample of alpha tocopherol acetate was obtained from Nutrition Square, Pittsburgh, Pennsylvania, said sample being certified to contain 1000 mg of alpha tocopherol acetate per gram. The sample was prepared as described above except that 12.9 mg of sample per 100 ml of methanol was used for absorbance measurements. The absorbancy was calculated as shown above for the alpha tocopherol sample, the values being set out in Table A, agreeing well with the alpha tocopherol acetate absorption maxima given in the *Merck Index* as 285.5 nm.

Comparison of the Table A data shows that the pure and mixed tocopherols demonstrate strong absorption of burning ultraviolet radiation in the 295–310 nm erythemal range, while the acetate is shown to be essentially non-absorbing in the erythemal range.

TABLE A

| Wavelength nm | Mixed Tocopherols Absorbance 26.3 mg/100 ml | Calc Absorbancy | Alpha Tocopherol Absorbance 15.7 mg/100 ml | Calc Absorbancy | Alpha Tocopherol Acetate Absorbance 12.9 mg/100 ml | Calc Absorbancy | |
|---|---|---|---|---|---|---|---|
| 400 | 0 | 0 | 0 | 0 | — | — | |
| 390 | 0 | 0 | 0 | 0 | — | — | |
| 380 | 0 | 0 | 0 | 0 | — | — | |
| 370 | 0 | 0 | 0 | 0 | — | — | |
| 360 | 0 | 0 | 0 | 0 | — | — | |
| 350 | 0 | 0 | 0 | 0 | 0 | 0 | |
| 340 | 0 | 0 | 0 | 0 | 0 | 0 | |
| 330 | 0 | 0 | 0.015 | 1.0 | 0 | 0 | |
| 320 | 0.040 | 2.8 | 0.02 | 1.3 | 0 | 0 | |
| 310 | 0.560 | 38.8 | 0.108 | 6.9 | 0 | 0 | |
| 305 | 1.12 | 77.5 | 0.418 | 26.6 | 0 | 0 | Erythemal range |
| 300 | 1.33 | 92.0 | 0.842 | 53.6 | 0.015 | 1.2 | |
| 295 | 1.36 | 94.1 | 1.113 | 70.9 | 0.06 | 4.7 | |
| 290 | 1.22 | 84.4 | 1.117 | 71.1 | 0.325 | 25.2 | |
| 285 | 0.937 | 64.8 | — | — | 0.50 | 38.8 | |
| 280 | 0.705 | 48.8 | 0.740 | 47.1 | 0.45 | 34.4 | |
| 270 | 0.367 | 25.5 | — | — | 0.26 | 20.2 | |
| 260 | | | | | 0.13 | 9.7 | |

EXAMPLE 2

Demonstration of the stability of mixed tocopherol ultraviolet absorbing properties when exposed to sunlight and air A 2.2-gram sample of Covi-Ox T-50, as described in Example 1, was poured into a plastic petri dish. The resulting thin film was placed in noon-time direct summer sunlight. Samples were withdrawn from the dish after ½, 1½ and 3½ hours exposure. Absorbance measurements were made on these samples, using isopropyl alcohol as the solvent and blank as in Example 1, and absorbancies calculated; the results are set out in Table B.

After 3½ hours of exposure, the sample was stored indoors, remaining exposed to air, and to indirect sunlight passing through a window. Further samples were taken for absorbance measurements after 4 days and 4 months. The measurements were made and the absorbancies calculated as in Example 1, the results additionally being set out in Table B.

As may be seen from Table B, exposure to sunlight and air for a period far in excess of that which an acceptable sunscreen as herein described must prove effective does not appreciably alter the absorption spectra or absorbancy of mixed tocopherols. While the tocopherols may have been chemically altered by exposure to sunlight and air, any such alteration apparently does not affect their ultraviolet absorption properties.

EXAMPLE 3

Comparison of the absorption spectra and absorbancy of commercially available suntan formulations with selective screens and sunscreen compositions comprising tocopherols Three commercial sunscreen preparations were secured: Coppertone Tanning Lotion containing homosalate as the screening agent; Sea and Ski Tanning Lotion with glycerol p-aminobenzoate as the screening agent; and Osco's Tanning Lotion with 2-ethoxyethyl-p-methoxycinnamate as the screening agent.

As in Example 1, 263 mg of each of these tanning preparations were weighed into a 100-ml volumetric flask. Methyl alcohol was added to each to make to volume. After dissolving, 10 ml of each of the solutions were pipetted into a 100-ml volumetric flask. Methyl alcohol was again added to bring the volume to 100 ml, each solution containing 26.3 mg of sample per 100 ml of alcohol.

Absorbance measurements were made on the Beckman DU-2 ultraviolet spectrophotometer, as in Example 1, between 280 to 350 nanometers. The absorbancy of these samples were calculated as follows:

$E_{1\,cm}^{1\%} = \text{absorbancy} = (A/B) \times C,$ where
A = 1000 mg/100 ml
B = sample weight
C = absorbance The results are set out in Table C.

Similarly, absorbance measurements were made and absorbancies calculated for a 47% alpha tocopherol sunscreen composition and a 14.8% mixed (alpha, beta, gamma and delta) tocopherol composition for comparative purposes; these results are set out in Table C.

As shown in Table C, the tocopherol sunscreens of the invention demonstrate superior absorbancies near the erythemal maxima at 297 nanometers in comparison to the commercial preparations containing prior art sunscreen compounds. The tocopherol sunscreens also demonstrate a superior cutoff at 310 nanometers, absorbing from 3 to 20 times less tanning radiation than the commercial sunscreen agents at 320 nanometers, and from 3 to 11 times less tanning radiation at 330 nanometers, while demonstrating no absorbance at 340 nanometers, as does the glycerol-p-aminobenzoate and 2-ethoxyethyl-p-methoxycinnamate.

TABLE B

| | Wavelength, nm | Absorbancy | | | | | |
|---|---|---|---|---|---|---|---|
| | | Exposed to Sunlight & Air | | | | Exposed to Air & Indirect Sunlight | |
| | | 0 hr | ½ hr | 1½ hr | 3½ hr | 4 days | 4 months |
| | 400 | 0 | 0 | 0 | 0 | — | — |
| | 390 | 0 | 0 | 0 | 0 | — | — |
| | 380 | 0 | 0 | 0 | 0 | — | — |
| | 370 | 0 | 0 | 0 | 0 | — | — |
| | 360 | 0 | 0 | 0 | 0 | — | — |
| | 350 | 0 | 0 | 0 | 0 | — | — |
| | 340 | 0 | 0 | 0.7 | 0.7 | — | — |
| | 330 | 0 | 0 | 1.2 | 1.1 | — | — |
| | 320 | 2.9 | 1.6 | 3.5 | 3.4 | — | 2.9 |
| Erythemal range | 310 | 38.5 | 42.2 | 39.6 | 40.0 | 33.4 | 20.5 |
| | 305 | 77.1 | 85.0 | 77.4 | 77.0 | 68.4 | 38.5 |
| | 300 | 91.6 | 92.4 | 93.4 | 93.8 | 85.4 | 45.5 |
| | 295 | 93.8 | 97.4 | 98.9 | 98.5 | 91.6 | 47.0 |
| | 290 | 84.0 | 88.4 | 90.9 | 90.1 | 84.0 | 42.7 |
| | 285 | 67.3 | 70.9 | 74.1 | 73.8 | — | — |
| | 280 | 48.7 | 54.9 | 57.4 | 57.1 | 53.1 | 26.9 |
| | 270 | 25.3 | 32.4 | 34.9 | 33.8 | — | — |

TABLE C

| | Wavelength, nm | Absorbancy | | | | |
|---|---|---|---|---|---|---|
| | | Homosalate | Glycerol-p-aminobenzoate | 2-ethoxyethyl-p-methoxycinnamate | Mixed tocopherols | Alpha tocopherol |
| | 350 | 0 | 0 | 0 | 0 | 0 |
| | 340 | 0 | 0.65 | 1.4 | 0 | 0 |
| | 330 | 1.8 | 1.2 | 6.6 | — | 0.47 |
| | 320 | 7.8 | 2.9 | 9.4 | 0.4 | 0.79 |
| | 310 | 12 | 7.5 | 11.7 | 5.7 | 3.2 |
| Erythemal range | 305 | 12.6 | 9.8 | 11.3 | 11.5 | 12.5 |
| | 300 | 11.6 | 12.1 | 11.1 | 13.7 | 25.2 |
| | 295 | 9.4 | 12.4 | 10.6 | 13.9 | 33.3 |
| | 290 | 7.8 | 12.4 | 10.0 | 12.5 | 33.4 |
| | 280 | 4.6 | 10.5 | 7.7 | 7.2 | 22.1 |

EXAMPLE 4

Demonstration of the Absorption Spectra and Absorbancy of Combined Tocopherol/Non-Tocopherol Sunscreen Compositions A sunscreen composition was formulated by adding 5 gm of a 15% mixed tocopherol alcoholic solution to 5 gm of a commercial tanning lotion containing 8% homosalate. The resulting formulation (A) comprised 4% homosalate, 7.5% mixed tocopherols and 88.5% vehicle. The absorbancy of formulation (A) was calculated from absorbance measurements made with a Beckman DU-2 spectrophotometer, using isopropyl alcohol as the solvent and blank, as described in Example 1. For comparative purposes, the absorbancy of the 8% homosalate lotion labeled formulation (B) was also calculated from absorbance measurements. The results are set out in column 1 of Table D, and show that the combined tocopherol-homosalate sunscreen formulation (A) exhibits improved absorbancy in the erythemal range, particularly near the 297 nm erythemal maxima, over that demonstrated by the homosalate formulation. Additionally, the tocopherol-homosalate formulation allows 50% more transmission of radiation in the tanning range than does the homosalate formulation.

Similarly, 5 gm of a 15% mixed tocopheral alcohol solution was added to 5 gm of a commercial tanning lotion containing 1.4% 2-ethoxyethyl-p-methoxycinnamate. The resulting formulation (C) comprised 0.7% 2-ethoxyethyl-p-methoxycinnamate, 7.5% mixed tocopherols and 91.8% vehicle. Absorbance measurements were taken and absorbancies calculated for formulation (C) and the 1.4% 2-ethoxyethyl-p-methoxycinnamate lotion denominated as formulation (D). These results are set out in column 2 of Table D. A further formulation (E) was also prepared from 1 gm of a 15% mixed tocopherol alcoholic solution and 1 gm of a commercial tanning lotion containing 2% glycerol-p-aminobenzoate so as to contain 1% glycerol-p-aminobenzoate, 7.5% mixed tocopherols, and 91.5% vehicle. Absorbance measurements were taken and absorbancies calculated for formulation (E) and the 2% glyceryl-p-aminobenzoate lotion denominated as formulation (F). These results are set out in column 3 of Table D.

As with the formulation (A) vs (B) comparison, comparison of formulations (C) vs (D) and (E) vs (F) shows improved absorbancy in the erythemal region, particularly near the 297 nm region, while allowing up to 50% more transmission of radiation in the tanning range, with the tocopherol/non-tocopherol formulations compared to the non-tocopherol formulations.

TABLE D

| | Wavelength nm | Absorbancy ($E_1^{\%}{}_{cm}$) | | | | | |
|---|---|---|---|---|---|---|---|
| | | A | B | C | D | E | F |
| | 350 | 0 | 0 | 0 | 0 | 0 | 0 |
| | 340 | 0 | 0 | 0.33 | 0.65 | 0.7 | 1.4 |
| | 330 | 0.9 | 1.8 | 0.6 | 1.2 | 3.3 | 6.6 |
| | 320 | 4.1 | 7.8 | 1.7 | 2.9 | 4.9 | 9.4 |
| | 310 | 8.9 | 12 | 6.7 | 7.5 | 8.9 | 11.7 |
| Erythemal range | 305 | 12.1 | 12.6 | 10.6 | 9.8 | 11.4 | 11.3 |
| | 300 | 12.8 | 11.6 | 13.1 | 12.1 | 12.6 | 11.1 |
| | 295 | 11.8 | 9.4 | 13.4 | 12.4 | 12.3 | 10.6 |
| | 290 | 10.1 | 7.8 | 12.5 | 12.4 | 11.3 | 10.0 |
| | 280 | 6.0 | 4.6 | 9.0 | 10.5 | 7.5 | 7.7 |

EXAMPLE 5

Demonstration of the Absorbance and Spectral Position of Absorption Bands of Thin Films of Typical Suntan Compositions Containing Tocopherols as the Sunscreen Alpha and mixed tocopherols were compounded into the following sunscreen compositions:

| Formulation A | | |
|---|---|---|
| 30 gm of Covi-Ox T-50 | 16.5% | mixed tocopherols |
| 70 gm coco butter | 13.5% | soybean oil |
| | 70% | coco butter |
| Formulation B | | |
| 30 gm of Covi-Ox T-50 | 16.5% | mixed tocopherols |
| 20 gm of coconut oil | 13.5% | soybean oil |
| 50 gm of coco butter | 20% | coconut oil |
| | 50% | coco butter |
| Formulation C | | |
| 30 gm of Covi-Ox T-50 | 16.5% | mixed tocopherols |
| 70 gm of water-oil emollients | 13.5% | soybean oil |
| | 70% | emollients (propylene glycol, glycerol stearate, stearic acid triethanol amine) |
| Formulation D | | |
| 45 gm alpha tocopherol | 45% | alpha tocopherol |
| 55 gm coco butter | 55% | coco butter |

The ingredients were mixed, with heating if necessary, to form solutions. Two matched 1-cm solid silica Beckman absorption cells having two frosted (etched) sides were utilized, each sample being smeared across the frosted sides so as to form a thin uniform film. The blank cell had a thin layer of glycerol spread over the frosted sides. These thin films caused the etched sides of the cells to become transparent.

Absorbance readings were taken on a Beckman DU-2 spectrophotometer, the absorbance of a 0.0025-mm layer being calculated as follows:

$$(M/a \text{ max}) \times (a) = a\ 0.0025 \text{ mm}$$

$$M = (A) \times 0.025 \text{ (or } E_{1\ cm}^{1\%} \times 0.025, \text{ as } E_{1\ cm}^{1\%}$$
$$= E_{0.1\ mm}^{100\%})$$

where
M = Absorbance of pure sample at its maxima in a 0.0025-mm cell
  M for mixed tocopherols = 2.35
  M for alpha tocopherols = 1.78
A = Absorbance of sample in alcohol at its maxima ($E_{1\ cm}^{1\%}$)
  A for mixed tocopherols = 94.1 at 295 nm
  A for alpha tocopherols = 71.1 at 290 nm
a max = measured absorbance of thin film sample at its maxima
  a max = 0.330 at 300 nm, formulation A
  a max = 0.23 at 300 nm, formulation B
  a max = 0.46 at 295 nm, formulation C
  a max = 0.88 at 300 nm, formulation D
a = measured absorbance of thin film of sample
a 0.0025 mm = calculated absorbance of a 0.0025-mm layer of unscreen formulation Table E contains the measured absorbance of the samples and the calculated $a0.0025$ value derived therefrom.

As may be seen from the Table E data, the absorption bands for thin films exhibit no change in spectral position, continuing to exhibit strong maxima in the erythemal region, particularly near the 297 nm erythemal maxima, and a sharp cutoff at 310 nm, the transition into the tanning area.

TABLE E

| | Wavelength, nm | A a | A $a_{.0025}$ | B a | B $a_{.0025}$ | C a | C $a_{.0025}$ | D a | D $a_{.0025}$ |
|---|---|---|---|---|---|---|---|---|---|
| | 340 | 0 | 0 | 0 | 0 | 0 | 0 | 0 | 0 |
| | 330 | 0 | 0 | 0.007 | 0.072 | 0.01 | 0.05 | 0 | 0 |
| | 320 | 0.05 | 0.36 | 0.02 | 0.20 | 0.03 | 0.15 | 0.11 | 0.22 |
| Erythemal | 310 | 0.18 | 1.28 | 0.14 | 1.38 | 0.27 | 1.37 | 0.22 | 0.44 |
| region | 305 | 0.31 | 2.19 | 0.22 | 2.2 | 0.42 | 2.14 | 0.66 | 1.35 |
| | 300 | 0.33 | 2.35 | 0.23 | 2.35 | 0.44 | 2.24 | 0.88 | 1.76 |
| | 295 | 0.32 | 2.31 | 0.23 | 2.35 | 0.46 | 2.45 | 0.88 | 1.76 |
| | 290 | 0.28 | 1.99 | 0.20 | 2.04 | 0.41 | 2.09 | 0.82 | 1.65 |
| | 280 | 0.15 | 1.10 | 0.12 | 1.28 | 0.31 | 1.58 | 0.55 | 1.10 |

EXAMPLE 6

Demonstration of the Incorporation of Tocopherols into Various Sunscreen Compositions The following compositions were prepared incorporating alpha and mixed tocopherols as the sunscreen agents:

A. Tanning butter: Into a 200-ml beaker, 30 gm of Covi-Ox T-50 mixed tocopherols and 70 gm of coco butter (from the Hershey Candy Company, Hershey, Pennsylvania) were added. The mixture was stirred and heated until a solution formed, then cooled to form a solid homogeneous mass.

B. Tanning cream: Into a 200-ml beaker, 30 gm of Covi-Ox T-50, 20 gm of coconut oil (Gentry International, Fairlawn, New Jersey), and 50 gm of coco butter were added. The mixture was stirred and heated until a solution formed, then 20 gm of ethyl alcohol was added. A suspension formed which thickened on cooling with constant stirring, forming a cream.

C. Tanning oil: Into a 200-ml beaker, 70 gm of coconut oil and 30 gm of Covi-Ox T-50 mixed tocopherols were added. The mixture was heated until a solution formed, which solution remaining stable at room temperature on cooling.

D. Tanning oil: To the oil of composition C was added 10 ml of ethyl alcohol, resulting in a less viscous solution which demonstrated a very refreshing feel to the skin on application.

E. Tanning oil: Into a 200-ml beaker, 45 gm of alpha tocopherol and 55 gm of coco butter were added. The mixture was heated until a solution formed, which solution remained stable at room temperature on cooling.

F. Tanning emulsion: 30 gm of Covi-Ox T-50 mixed tocopherols were added to 70 gm of Osco Tanning Lotion, which was a water-oil emulsion consisting of water, stearic acid, glycerol stearate, isopropyl myristate, sesame oil, triethanolamine, cetyl alcohol, Ethoxin, perfume, T.E.A. lauryl sulfate, methyl paraben and propyl paraben, to form an emulsion.

G. Tanning emulsion:

| | S | |
|---|---|---|
| Part A: | alpha tocopherol | 25 gm |
| | stearic acid | 10 gm |
| | methyl phenyl siloxane | 10 gm |
| | glycerol monostearate | 5 gm |
| | butylated hydroxytoluene | 0.1 gm |
| Part B: | water | 45 gm |
| | propylene glycol | 4 gm |
| | triethanolamine | 1 gm |

The part A ingredients were added together and heated until a solution formed; part B ingredients were similarly added together. The warm part A ingredients were added to the part B ingredients with rapid agitation, forming an emulsion.

H. Tanning solution (alcoholic):

| | |
|---|---|
| Covi-Ox T-50 mixed tocopherols | 15 gm |
| Soybean oil | 15 gm |
| Dimethyl siloxane | 10 gm |
| Isopropyl alcohol | 60 gm |
| BHT | 0.1 gm |

The dimethyl siloxane was dissolved in the Covi-Ox T-50 and soybean oil, and the resulting solution added to the alcohol to form a clear, stable solution.

I. Tanning butter:

| | |
|---|---|
| Alpha tocopherol | 15 gm |
| Dimethyl siloxane | 3 gm |
| Sea and Ski Tanning Butter* | 82 gm |

*From Sea and Ski Corp., Reno, Nevada; contains acetylated lanolin, ceresin, isopropyl lanolate, mineral oil, polysorbate 60, coco butter, coconut oil, petrolatum, BHA, BHT, citric acid, butylparaben and fragrance.

The siloxane was added to the alpha tocopherols, the resulting solution then added to the tanning butter. This combination was heated and a solution was formed which gelled into a butter on cooling.

EXAMPLE 7

Demonstration of the Efficacy of Tocopherol-Containing Sunscreen Compositions to Reduce Erythema While Permitting Tanning by Field Testing Part 1

Five rectangular cuts 1 inch × 3 inches were made on the back of a black pullover sweatshirt. Four subjects were utilized: an adult male, an adult female, and two children below the age of ten, one male and one female. The sweatshirt was put on each of the subjects, and films of compositions E, G, H, and I, as described in Example 6, were applied to the backs of the subjects through the slots in the shirt. No preparation was placed on the subject back through the fifth slot, which served as the control.

The back of each subject was then irradiated, while still wearing the black sweatshirt, with a Westinghouse 275W sunlamp (with reflector) at a distance of 10 inches. The adults were each exposed for 10 minutes, the children for 7 minutes. The outlines of each slot were marked on each subject's back by means of an indelible marker.

Eight hours after exposure, the slotted areas were examined. Each control area on the backs of the subjects showed mild erythema, while none of the four preparation-treated areas showed any erythema.

This procedure was repeated four times, with the same results on each repetition.

Part 2

Utilizing the procedures set out in part 1, the adult male was irradiated with the Westinghouse sunlamp for 30 minutes. Ten hours later, severe erythema was visible in the control area. No erythema, or mild erythema, was visible in the areas protected with preparations E, G, H and I. Three days later, the control area blistered severely, and the skin peeled. There was no evidence of blistering or peeling in the protected areas.

Part 3

The face of the adult male was irradiated for 15-minute intervals utilizing the Westinghouse 250W sunlamp at a ten (10) inch distance on six occasions, each irradiation separated by a one-week period from the previous exposure. Each of preparations E, G, H and I was applied to the subject's face at least once during the 6-week test cycle.

No vivid erythema occurred to the subject's face during or after the tests; the subject's face developed an even tan which persisted for a two-week period after conclusion of the test cycle.

Part 4

A sunscreen formulation containing 11% by weight mixed tocopherols, the remaining 89% by weight being mineral and vegetable oils, was prepared. An adult male subject applied the formulation to the right leg, right half of his abdomen and chest, and his entire neck and face. The left leg and left half of the abdomen and chest were left unprotected to serve as a control.

The subject was exposed to bright, direct summer sunlight for 1 hour. Several hours later, the control and experimental parts of the body were compared: the control area was moderately red and tender, the experimental part faintly red and not tender.

This procedure was repeated the following day, save that the subject was exposed to bright, direct summer sunlight for 3 hours. Several hours later, comparison of the body areas showed the control to be intensely red and moderately tender; the experimental area was slightly red and much less tender than the control. Comparison of the exposed areas of the subject, both experimental and control, to non-exposed areas showed both the control and experimental parts to be decidedly more tan than the unexposed areas.

While particular embodiments of the invention have been shown, it will be understood, of course, that the invention is not limited thereto since modifications may be made by those skilled in the art, particularly in light of the foregoing teachings. It is, therefore, comtemplated by the appended claims to cover any such modifications as incorporate those features which constitute the essential features of these improvements within the true spirit and the scope of the invention.

I claim:

1. A method of preventing erythema of the skin caused by the absorption of burning ultraviolet radiation resulting from exposure to natural or artificial sources thereof while concomitantly allowing tanning of the skin consisting of the application of a sunscreen composition demonstrating selective ultraviolet radiation absorption in the 295-315 nanometer wavelength range prior to exposure of the skin to said radiation source, said composition comprising a sunscreen-effective amount of an ultraviolet-absorbing tocopherol compound selected from the group consisting of alpha tocopherol, beta tocopherol, gamma tocopherol, delta tocopherol, epsilon tocopherol, zeta tocopherol, eta tocopherol and mixtures thereof, and an inert carrier vehicle for said tocopherol compound, said vehicle being non-toxic and non-irritating to the skin.

2. The method according to claim 1 wherein said tocopherol compound is alpha tocopherol.

3. The method according to claim 1 wherein said tocopherol compound is a mixture consisting essentially of alpha, beta, gamma and delta tocopherol.

4. The method according to claim 1 wherein said carrier vehicle is selected from the group consisting of water, mineral oil, vegetable oil, petrolatum, silicone oil, alcohol and mixtures thereof.

5. The method according to claim 1 wherein said preparation additionally comprises a component selected from the group consisting of butylated hydroxytoluene, butylated hydroxyanisole, propyl gallate, a triethanolamine fatty acid salt, an isopropyl amine fatty acid salt, ethylenediaminetetraacetic acid the disodium salt of ethylenediaminetetraacetic acid, a citric acid fatty acid ester, an ascorbic acid fatty acid ester, and mixtures thereof.

6. The method according to claim 2 wherein said composition contains at least about 10% by weight alpha tocopherol.

7. The method according to claim 3 wherein said composition contains at least about 4.5% by weight of a mixture consisting essentially of alpha, beta, delta and gamma tocopherol.

8. The method according to claim 5 wherein said tocopherol compound is alpha tocopherol, said composition containing at least about 10% by weight thereof.

9. The method according to claim 5 wherein said tocopherol compound is a mixture consisting essentially of alpha, beta, delta and gamma tocopherol, said composition containing at least about 4.5% by weight thereof.

10. The method according to claim 1 wherein said composition comprises a sunscreen effective amount of a sunscreen agent consisting of at least 50% by weight of an ultraviolet-absorbing tocopherol compound as a major component and a non-tocopherol ultraviolet-absorbing compound as a minor component thereof, said tocopherol compound being further selected from the group consisting of alpha tocopherol, beta tocopherol, gamma tocopherol, delta tocopherol, epsilon tocopherol, zeta tocopherol, eta tocopherol and mixtures thereof.

11. The method according to claim 10 wherein said non-tocopherol ultraviolet-absorbing compound is selected from the group consisting of a salicylates, a para-aminobenzoates, a benzophenone, a cinnamate, a naphthoate, a gallate and mixtures thereof.

12. The method according to claim 10 wherein said tocopherol compound is alpha tocopherol.

13. The method according to claim 10 wherein said tocopherol compound is a mixture consisting essentially of alpha, beta, gamma and delta tocopherol.

14. The method according to claim 10 wherein said carrier vehicle is selected from the group consisting of water, mineral oil, vegetable oil, petrolatum, silicone oil, alcohol, and mixtures thereof.

15. The method according to claim 10 wherein said composition additionally comprises a component selected from the group consisting of butylated hydroxytoluene, butylated hydroxyanisole, propyl gallate, a triethanolamine fatty acid salt, an isopropyl amine fatty acid salt, ethylenediaminetetraacetic acid the disodium salt of ethylenediaminetetraacetic acid, a citric acid fatty acid ester, an ascorbic acid fatty acid ester, and mixtures thereof.

16. The method according to claim 12 wherein said composition contains at least about 5% by weight alpha tocopherol.

17. The method according to claim 13 wherein said composition contains at least about 2.3% by weight of a mixture consisting essentially of alpha, beta, delta and gamma tocopherol.

18. The method according to claim 15 wherein said tocopherol compound is alpha tocopherol, said composition containing at least about 5% by weight thereof.

19. The method according to claim 15 wherein said tocopherol compound is a mixture consisting essentially of alpha, beta, delta and gamma tocopherol, said composition containing at least 2.3% by weight thereof.

20. A sunscreen composition comprising a sunscreen effective amount of a sunscreen agent consisting of at least 50% by weight of an ultraviolet-absorbing tocopherol compound as a major component and a non-tocopherol ultraviolet-absorbing compound as a minor component thereof,
   said tocopherol compound being further selected from the group consisting of alpha tocopherol, beta tocopherol, gamma tocopherol, delta tocopherol, epsilon tocopherol, zeta tocopherol, eta tocopherol and mixtures thereof,
   said non-tocopherol ultraviolet-absorbing compound being further selected from the group consisting of a salicylate, a para-aminobenzoate, a benzophenone, a cinnamate, a naphthoate, a gallate, and mixtures thereof,
   and an inert carrier vehicle for said agent, said vehicle being non-toxic and non-irratating to the skin.

21. The sunscreen composition according to claim 20 wherein said composition additionally comprises a component selected from the group consisting of butylated hydroxytoluene, butylated hydroxyanisole, propyl gallate, a triethanolamine fatty acid salt, an isopropyl amine fatty acid salt, ethylenediaminetetraacetic acid the disodium salt of ethylenediaminetetraacetic acid, a citric acid fatty acid ester, an ascorbic acid fatty acid ester, and mixtures thereof.

22. The sunscreen composition according to claim 20 wherein said carrier vehicle is selected from the group consisting of water, mineral oil, vegetable oil, petrolatum, silicone oil, alcohol, and mixtures thereof.

23. The sunscreen composition according to claim 21 wherein said carrier vehicle is selected from the group consisting of water, mineral oil, vegetable oil, petrolatum, silicone oil, alcohol, and mixtures thereof.

24. The sunscreen composition according to claim 21 wherein said composition contains at least about 5% by weight alpha tocopherol.

25. The sunscreen composition according to claim 21 wherein said composition contains at least 2.3% by weight of a mixture consisting essentially of alpha, beta, delta and gamma tocopherol.

26. The sunscreen composition according to claim 23 wherein said composition contains at least 2.3% by weight of a mixture consisting essentially of alpha, beta, delta and gamma tocopherol.

* * * * *

UNITED STATES PATENT AND TRADEMARK OFFICE
CERTIFICATE OF CORRECTION

PATENT NO. : 4,144,325
DATED : March 13, 1979
INVENTOR(S) : Walter F. Voyt

It is certified that error appears in the above-identified patent and that said Letters Patent are hereby corrected as shown below:

Table C, bottom of Column 12, heading, change

"2-ethoxyethyl-p-methoxycinnamamate" to read -- 2-ethoxyethyl-p-methoxycinnamate --

Column 13, line 28:

change "mixed tocopheral" to read

-- mixed tocopherol --

Column 14, line 20:

change "stearic acid triethanol" to read

-- stearic acid, triethanol --

UNITED STATES PATENT AND TRADEMARK OFFICE
CERTIFICATE OF CORRECTION

PATENT NO. : 4,144,325

DATED : March 13, 1979

INVENTOR(S) : Walter F. Voyt

It is certified that error appears in the above-identified patent and that said Letters Patent are hereby corrected as shown below:

line 37:

change "(M/a max) x(a) = a 0.0025mm" to read -- $(M/a_{max}) \; x(a) = a_{0.0025mm}$ -- line 50:

change "at 290 nm" to read -- at 294 nm -- lines 51-56:

change "a max" to read -- $a_{max}$ -- line 58:

change "a 0.0025 mm" to read -- $a_{0.0025mm}$ --

UNITED STATES PATENT AND TRADEMARK OFFICE
CERTIFICATE OF CORRECTION

PATENT NO. : 4,144,325

DATED : March 13, 1979

INVENTOR(S) : Walter F. Voyt

It is certified that error appears in the above-identified patent and that said Letters Patent are hereby corrected as shown below:

line 59:

change "unscreen" to read -- sunscreen --

Column 15, line 55:

delete "S" at center of Table

Column 17, line 49:

change "comtem-" to read -- contem --

UNITED STATES PATENT AND TRADEMARK OFFICE
CERTIFICATE OF CORRECTION

PATENT NO. : 4,144,325

DATED : March 13, 1979

INVENTOR(S) : Walter F. Voyt

It is certified that error appears in the above-identified patent and that said Letters Patent are hereby corrected as shown below:

Column 18, lines 15 et seq., claim 5: change

"propyl gallate, a triethanolamine fatty acid salt, an isopropyl amine fatty acid salt, ethylenediaminetetraacetic acid the disodium salt of ethylenediaminetetraacetic acid, a citric acid fatty acid ester, an ascorbic acid fatty acid ester" to read -- propyl gallate, triethanolamine, a triethanolamine fatty acid salt, isopropyl amine, an isopropyl amine fatty acid salt, ethylenediaminetetraacetic acid, the disodium salt of ethylenediaminetetraacetic acid, citric acid, a citric acid fatty acid ester, ascorbic acid, an ascorbic acid fatty acid ester --

UNITED STATES PATENT AND TRADEMARK OFFICE
CERTIFICATE OF CORRECTION

PATENT NO. : 4,144,325
DATED : March 13, 1979
INVENTOR(S) : Walter F. Voyt

It is certified that error appears in the above-identified patent and that said Letters Patent are hereby corrected as shown below:

lines 50-51, claim 11: change "of a salicylates, a para-aminobenzoates," to read -- a salicylate, a para-aminobenzoate, -- lines 65, et seq., claim 15: change "propyl gallate, a triethanolamine fatty acid salt, an isopropyl amine fatty acid salt, ethylenediaminetetraacetic acid the disodium salt of ethylenediaminetetraacetic acid, a citric acid fatty acid ester, an ascorbic acid fatty acid ester" to read -- propyl gallate, triethanolamine, a triethanolamine fatty acid salt, isopropyl amine, an isopropyl amine fatty acid salt, ethylenediaminetetraacetic acid, the disodium salt of ethylenediaminetetraacetic acid, citric acid, a citric acid fatty acid ester, ascorbic acid, an ascorbic acid fatty acid ester --

UNITED STATES PATENT OFFICE
CERTIFICATE OF CORRECTION

Patent No. 4,144,325     Dated  March 13, 1979

Inventor(s) Walter F. Voyt

It is certified that error appears in the above-identified patent and that said Letters Patent are hereby corrected as shown below:

Column 20, line 4, claim 20:  change "non-irratating"

to read -- non-irritating -- lines 8 et seq., claim 21:  change

"propyl gallate, a triethanolamine fatty acid salt, an isopropyl amine fatty acid salt, ethylenediaminetetraacetic acid the disodium salt of ethylenediaminetetraacetic acid, a citric acid fatty acid ester, an ascorbic acid fatty acid ester"

UNITED STATES PATENT OFFICE
CERTIFICATE OF CORRECTION

Patent No. 4,144,325　　　　　　　　Dated　March 13, 1979

Inventor(s)　Walter F. Voyt

It is certified that error appears in the above-identified patent and that said Letters Patent are hereby corrected as shown below:

to read -- propyl gallate, triethanolamine, a triethanolamine fatty acid salt, isopropyl amine, an isopropyl amine fatty acid salt, ethylenediaminetetraacetic acid, the disodium salt of ethylenediaminetetraacetic acid, citric acid, a citric acid fatty acid ester, ascorbic acid, an ascorbic acid fatty acid ester --

Signed and Sealed this

Twenty-third Day of October 1979

[SEAL]

*Attest:*

RUTH C. MASON
*Attesting Officer*

LUTRELLE F. PARKER
*Acting Commissioner of Patents and Trademarks*